United States Patent
Rane

(10) Patent No.: US 9,592,208 B2
(45) Date of Patent: Mar. 14, 2017

(54) FORMULATIONS COMPRISING 2-AMINO-2-[2-(4-OCTYLPHENYL)ETHYL]PROPANE-1,3-DIOL

(75) Inventor: Supriya Rane, Parsippany, NJ (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 14/009,241

(22) PCT Filed: Mar. 30, 2012

(86) PCT No.: PCT/US2012/031340
§ 371 (c)(1),
(2), (4) Date: Oct. 1, 2013

(87) PCT Pub. No.: WO2012/135561
PCT Pub. Date: Oct. 4, 2012

(65) Prior Publication Data
US 2014/0371323 A1 Dec. 18, 2014

Related U.S. Application Data

(60) Provisional application No. 61/545,835, filed on Oct. 11, 2011, provisional application No. 61/470,747, filed on Apr. 1, 2011.

(51) Int. Cl.
| | | |
|---|---|---|
| *A61K 31/137* | (2006.01) | |
| *A61K 47/40* | (2006.01) | |
| *A61K 9/48* | (2006.01) | |
| *A61K 9/20* | (2006.01) | |
| *A61K 31/661* | (2006.01) | |
| *A61K 9/16* | (2006.01) | |

(52) U.S. Cl.
CPC .......... *A61K 31/137* (2013.01); *A61K 9/1652* (2013.01); *A61K 9/205* (2013.01); *A61K 9/4808* (2013.01); *A61K 9/4866* (2013.01); *A61K 31/661* (2013.01); *A61K 47/40* (2013.01)

(58) Field of Classification Search
CPC .... A61K 9/1652; A61K 31/137; A61K 9/205; A61K 47/40; A61K 9/4866; A61K 31/661; A61K 9/4808
USPC .................................................. 514/769, 653
See application file for complete search history.

(56) References Cited

U.S. PATENT DOCUMENTS

| 5,604,229 | A | 2/1997 | Chiba | |
|---|---|---|---|---|
| 6,476,004 | B1 | 11/2002 | Sakai | |
| 7,888,527 | B2 | 2/2011 | Lynch et al. | |
| 2004/0048877 | A1* | 3/2004 | Friedl et al. | 514/254.06 |
| 2008/0311188 | A1* | 12/2008 | Oomura et al. | 424/452 |

FOREIGN PATENT DOCUMENTS

| EP | 0990440 A1 | 4/2000 |
|---|---|---|
| EP | 1002792 A1 | 5/2000 |
| EP | 1050301 A1 | 11/2000 |
| EP | 1982708 A1 | 10/2008 |
| WO | 9408943 A1 | 4/1994 |
| WO | 0218395 A1 | 3/2002 |
| WO | 2004089341 A1 | 10/2004 |
| WO | WO 2005/025553 A2 | 3/2005 |
| WO | WO 2005025553 A2 * | 3/2005 |
| WO | 2007/021666 A2 | 2/2007 |
| WO | WO 2008/037421 A2 | 4/2008 |
| WO | 2008/079382 A1 | 7/2008 |
| WO | 2009/048993 A2 | 4/2009 |
| WO | 2010/055027 A2 | 5/2010 |
| WO | 2010/075239 A1 | 7/2010 |

OTHER PUBLICATIONS

Loftsson, T.,"Pharmaceutical applications of cyclodextrins. 1. Drug solubilization and stabilization." Journal of pharmaceutical sciences 85.10 (1996): 1017-1025.*
Pinkel, D.,"The use of body surface area as a criterion of drug dosage in cancer chemotherapy." Cancer Research 18.7 (1958): 853-856.*
Diem, R., "Neurodegeneration and -protection in autoimmune CNS inflammation." Journal of neuroimmunology 184.1 (2007): 27-36.*
Mayo Clinic Diseases and Conditions, 2014—Multiple Sclerosis Causes p. 1-8.;accessed online Jul. 8, 2015; http://www.mayoclinic.org/diseases-conditions/multiple-sclerosis/basics/definition/con-20026689.*
Multiple Sclerosis Information Page NINDS-NIH, p. 1-3; accessed online Jul. 8, 2015 http://www.ninds.nih.gov/disorders/multiple_sclerosis/multiple_sclerosis.htm.*
Rower et al., "Handbook of Pharmaceutical Excipients", Edition 6, Pharmaceutical Press. 2009, pp. 211-214.
Andean Patent Manuel, OMPI-EPO, Andean Community Secretary, 2004, ISBN-9978-43-855-6, Section 10.8.1.
Ueda, "Possible use of cyclodextrins in pharmaceutical preparations", Proc. Hoshi University, 1992, No. 34, p. 7, lines 6-11, English translation.
Miller, "Practical Considerations in Development of Solid dosage Forms that Contain Cyclodextrin", Journal of Pharmaceutical Sciences, vol. 96, No. 7, pp. 1691-1707, (Jul. 2007).
Disclosed anonymously, "Solid State Forms of 2-amino-2-[2-4-octylphenyl)ethyl]-1,3-propanediol hydrochloride", IP.com Journal, IP.COM Inc., West Henrietta, NY, US, (Mar. 3, 2011). XP013148489.
Loftsson et al., "Pharmaceutical Applications of Cyclodextrins. 1. Drug Solubilization and stabilization", Journal of Pharmaceutical Sciences, vol. 85, No. 10, pp. 1017-1025, (Oct. 1, 1996). XP002080430.

* cited by examiner

*Primary Examiner* — Samantha Shterengarts
*Assistant Examiner* — Matt Mauro
(74) *Attorney, Agent, or Firm* — Andrew Holmes

(57) ABSTRACT

A solid pharmaceutical composition suitable for oral administration, comprising:
(a) a S1P receptor modulator;
(b) a filler, and
(c) a cyclodextrin.

11 Claims, No Drawings

FORMULATIONS COMPRISING 2-AMINO-2-[2-(4-OCTYLPHENYL)ETHYL] PROPANE-1,3-DIOL

This application is a 371 of PCT/EP2012/031340 filed on Mar. 30, 2012 which claims benefit of U.S. Provisional Application No. 61/470,747 filed on Apr. 1, 2011 and U.S. Provisional Application No. 61/545,835 filed on Oct. 11, 2011, which in their entirety are herein incorporated by reference.

The present invention relates to pharmaceutical compositions comprising a S1P receptor modulator selected from 2-amino-2-[2-(4-octylphenyl)ethyl]propane-1,3-diol in free form, in a pharmaceutically acceptable salt form (fingolimod, FTY720) and a phosphate derivative thereof (FTY720-phosphate), as well as process for their production and use of the pharmaceutical compositions.

2-amino-2-[2-(4-octylphenyl)ethyl]propane-1,3-diol hydrochloride became the first oral drug approved to reduce relapses and delay disability progression in patients with relapsing forms of multiple sclerosis (MS). Before, the MS drugs on the markets were all delivered by frequent injections, either intravenously or intra-muscularly, varying from once-per-day to once-per-week depending on the drug.

Fingolimod is believed to reduce the number of lymphocytes circulating in the blood stream by reversibly trapping a proportion of them in the lymph nodes. Consequently, the number of activated lymphocytes reaching the brain is decreased, resulting in reduced inflammatory destruction. Fingolimod efficacy in the treatment of multiple sclerosis has been shown in humans (e.g. as described in "FTY720 therapy exerts differential effects on T cell subsets in multiple sclerosis". Mehling M, et al., Neurology. 2008 Oct. 14; 71(16):1261-7; and "Oral fingolimod (FTY720) for relapsing multiple sclerosis". Kappos L, Antel J, Comi G, Montalban X, O'Connor P, Polman C H, Haas T, Korn A A, Karlsson G, Radue E W; FTY720 D2201 Study Group. N Engl J. Med. 2006 Sep. 14; 355(11):1124-40.).

Pharmaceutical compositions comprising 2-amino-2-[2-(4-octylphenyl)ethyl]propane-1,3-diol in free form or in a pharmaceutically acceptable salt form (fingolimod) or as a phosphate derivative, in particular in form of oral formulations, are known in the art, e.g. as described in EP1613288A the content of which being incorporated herein by reference. EP1613288A describes a tablet comprising 1.4 mg of the hydrochloride salt of 2-amino-2-[2-(4-octylphenyl)ethyl] propane-1,3-diol, and capsules comprising 0.56 mg, 1.0 mg or more of the hydrochloride salt of 2-amino-2-[2-(4-octylphenyl)ethyl]propane-1,3-diol.

Solid state forms of 2-amino-2-[2-(4-octylphenyl)ethyl] propane-1,3-diol hydrochloride are described in the art. For example, IPCOM000204549D describes crystals of 2-amino-2-[2-(4-octylphenyl)ethyl]propane-1,3-diol hydrochloride prepared by mixing about 30 wt % of 2-amino-2-[2-(4-octylphenyl)ethyl]propane-1,3-diol hydrochloride with about 75 wt % α- or β-cyclodextrin in water and then evaporating water with ethanol to dryness, and drying the solid. There is no indication of using a low amount of 2-amino-2-[2-(4-octylphenyl) ethyl]propane-1,3-diol hydrochloride as in the present invention, even less preparing a composition comprising a low amount of 2-amino-2-[2-(4-octylphenyl)ethyl]propane-1,3-diol hydrochloride which complies with all the requirements of a pharmaceutical compositions, as now obtained with the compositions of the present invention.

However there still exists a need for preparing an improved pharmaceutical composition for oral administration containing 2-amino-2-[2-(4-octylphenyl)ethyl]propane-1,3-diol, in free form, in a pharmaceutically acceptable salt form or as a phosphate derivative. In particular there is a need for preparing a pharmaceutical composition which can be used to administer on a safe and prolonged way a low amount of the compound, i.e. a composition which is stable, homogeneous and shows appropriate content uniformity, while containing 0.5 mg or less of 2-amino-2-[2-(4-octylphenyl)ethyl]propane-1,3-diol.

Obtaining a composition that is stable, homogeneous, e.g. which shows appropriate blend content uniformity and/or drug content uniformity is particularly critical for a composition containing a low amount of the active substance since in such a case even minor modifications on the drug amount, e.g. due to degradation or lack of uniformity, may lead to be a significant impact on the total content of the drug that the patient consumes. With a limited amount of drug in the composition, even a limited degradation thereof may result in administering to the patient a drug amount that is too low to provide the desired therapeutic benefit. So it may be paramount for the patient to receive the adequate drug dosage every time he (or she) is taking his (or her) medication in order to ensure long term efficacy of the drug. The lower the drug content is, the more these requirements are difficult to meet. For example, it can be shown that the stability of solid composition comprising fingolimod is dependent upon the concentration of the drug, and therefore the lower the concentration of the compound, the more it becomes sensitive to degradation.

Furthermore, when formulating an oral composition containing 2-amino-2-[2-(4-octylphenyl) ethyl]propane-1,3-diol, in free form, in a pharmaceutically acceptable salt form or as a phosphate derivative, the person skilled in the art is confronted with several difficulties due to the nature and characteristics of the compound. Fingolimod is instable in presence of many excipients, especially at high temperatures or humidity conditions: many pharmaceutically acceptable excipients are not compatible with fingolimod, i.e. when mixed thereto induce impurities or degradation products at a level above the acceptable level for a pharmaceutical composition, according to the Regulatory Health Authorities. Fingolimod, in particular when micronized, is also static in nature and has the tendency to stick to metal surfaces, leading to non negligible drug segregation during the formulation manufacture. This may pose problems when preparing large scales of fingolimod-containing compositions, in particular compositions comprising low dosage of the drug, for example 0.5 mg or less.

It has now been found that by using a stabilizer, for example a cyclodextrin, it becomes possible to prepare pharmaceutical compositions for oral administration comprising a low amount of 2-amino-2-[2-(4-octylphenyl)ethyl] propane-1,3-diol, in free form, in a pharmaceutically acceptable salt form or as a phosphate derivative, which show an appropriate content uniformity and are physically stable even during extended periods of time. In particular it has become possible to prepare stable compositions comprising less than 0.5 mg of 2-amino-2-[2-(4-octylphenyl)ethyl]propane-1,3-diol, e.g. 0.25 mg or less. Unexpectedly, despite the low amount of 2-amino-2-[2-(4-octylphenyl)ethyl]propane-1,3-diol, the interaction of fingolimod with the other excipients that are needed for preparing a solid composition for oral administration are now minimized.

Furthermore, the segregation which otherwise occurs during the manufacturing process and leads to a partial loss of the drug substance, is reduced. Thus compositions comprising a low amount of 2-amino-2-[2-(4-octylphenyl)ethyl]

propane-1,3-diol, e.g. 0.5 mg or less, can be prepared on large scales with limited variations in the drug content amongst the different batches.

In particular, the use of a stabilizer, for example a cyclodextrin or derivative thereof, in the formulation process permits blending of the different ingredients (active substance and excipients) in such a way that a mixture of uniform particle size is obtained and thus an even distribution of the drug content in the final composition is ensured.

The invention provides solid pharmaceutical compositions suitable for oral administration, and comprising
a) a compound selected from 2-amino-2-[2-(4-octylphenyl)ethyl]propane-1,3-diol, a pharmaceutically acceptable salt thereof, and a phosphate derivative thereof,
b) a filler,
c) a stabilizer, and optionally
d) a binder and/or a lubricant.

The compound of the invention is selected from 2-amino-2-[2-(4-octylphenyl)ethyl]propane-1,3-diol in free form, a pharmaceutically acceptable salt thereof, and a phosphate derivative thereof, e.g. is 2-amino-2-[2-(4-octylphenyl)ethyl]propane-1,3-diol in free form or a pharmaceutically acceptable salt thereof.

The structure of 2-amino-2-[2-(4-octylphenyl)ethyl]propane-1,3-diol (FTY720) is shown below:

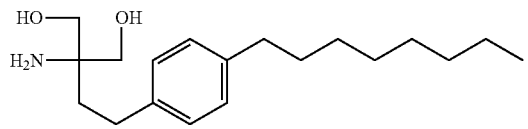 [SMILES: CCCCCCCCc1ccc(CCC(N)(CO)CO)cc1]

The structure of phosphate derivative thereof is shown below:

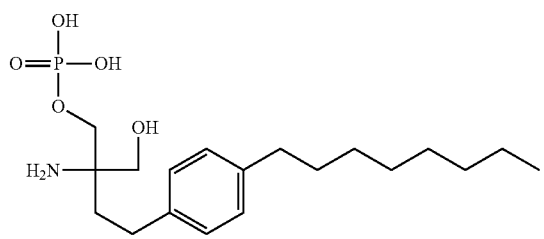 [SMILES: CCCCCCCCc1ccc(CCC(N)(CO)COP(=O)(O)O)cc1]

According to the present invention, the compound may be a salt selected from ascorbate, oxalate, phosphate, mandelate, adipate, ethanesulfonate, naphtalene-1,5-disulfonate, naphtalene-1-sulfonate, naphtalene-2-sulfonate, aspartate, e.g. L-aspartate, benzoate, 4-acetamidobenzoate, (+) camphorate, (+)camphor-10-sulfonate, decanoate, hexanoate, octanoate, cinnamate, dodecylsulfate, ethane-1,2-disulfonate, 2-hydroxyethanesulfonate, glutarate, lactate, e.g. DL-lactate, 1-hydroxy-2-naphthoate, laureate, salicylate, hydrochloride, tartrate, mesylate, citrate, benzoate, succinate, malonate, acetate, propionate salts and mixture thereof. The salt is optionally crystalline.

In one specific embodiment of the invention, the salt is hydrochloride.

The composition of the invention may contain 0.01 to 20% by weight of the compound of the invention, for example 0.1 to 10%, e.g. 0.05 to 10%, e.g. 0.05 to 5%, e.g. 0.05 to 2%, e.g. 0.1 to 5%, e.g. 0.1 to 2%, e.g. 0.1 to 5%, e.g. 0.1 to 2%, e.g. 0.5 to 5%, e.g. 0.5 to 2%, e.g. 0.8 to 1.3%, e.g. 0.9 to 1.2%, by weight, based on the total weight of the composition, or e.g. 0.1 to 0.5%, e.g. 0.15 to 0.5, e.g. 0.2 to 0.3% by weight, based on the total weight of the composition. For example, the composition of the invention comprises about 1% by weight of the S1P receptor modulator, based on the total weight of the composition, for example 1% by weight plus or less 0.15% of the S1P receptor modulator, based on the total weight of the composition. For example about 0.6% by weight, for example about 0.5% by weight, for example about 0.4% by weight, for example about 0.3% by weight, for example about 0.25% by weight, for example about 0.2% by weight, for example about 0.15% by weight, based on the total weight of the composition. In another example, the composition of the invention comprises less than 2% by weight, less than 1.5% by weight, less than 1% by weight of the S1P receptor modulator, e.g. less than 0.5% by weight, e.g. less than 0.4% by weight e.g. less than 0.3% by weight, e.g. less than 0.2% by weight, based on the total weight of the composition According to the invention, the stabilizer may be selected from a cyclodextrin or a derivative thereof, glycine HCl, sodium bicarbonate, and mixture thereof. In one embodiment of the invention, the stabilizer comprises a cyclodextrin or a derivative thereof, or consists of a cyclodextrin or a derivative thereof, e.g. as herein below defined.

Under cyclodextrin and derivative thereof it is meant e.g. a natural cyclodextrin, a branched cyclodextrin, an alkyl-cyclodextrin or a hydroxyalkyl-cyclodextrin. For example cyclodextrin or and derivative thereof may be α-cyclodextrin; β-cyclodextrin, γ-cyclodextrin; hydroxypropyl-cyclodextrin such as hydroxypropyl-α-cyclodextrin or hydroxypropyl-β-cyclodextrin; sulfobutylether β-cyclodextrin; dodecakis-2,6,O-methyl-α-cyclodextrin; tetradecakis-2,6,O-methyl-β-cyclodextrin; hexadecakis-2,6,O-methyl-γ-cyclodextrin; tetradecakis-2,6,O -ethyl-β-cyclodextrin; α-cyclodextrin partially etherized with 2-hydroxypropyl; β-cyclodextrin partially etherized with 2-hydroxypropyl; branched α-cyclodextrin and branched β-cyclodextrin where glucose or maltose has been bound via α-1,6 glucoside bound.

In a specific embodiment of the invention, cyclodextrin or derivative thereof is hydroxypropyl-α-cyclodextrin or hydroxypropyl-β-cyclodextrin, e.g. hydroxypropyl-β-cyclodextrin (also herein referred as HP-β CD).

In another embodiment of the invention, cyclodextrin and derivative thereof is not α-cyclodextrin nor β-cyclodextrin.

The composition of the invention, e.g. the final product for oral administration or an intermediate form thereof. may contain 0.1 to 30%, e.g. 0.2 to 15% by weight of the stabilizer, e.g. cyclodextrin or a derivative thereof, for example 0.4 to 10%, e.g. 0.5 to 10%, e.g. 0.6 to 10%, e.g. 1.5 to 8% or 1.5 to 3.5%, e.g. 1.0 to 5% or 1.0 to 3%, e.g. 0.1 to 10%, e.g. 0.1 to 8%, e.g. 0.1 to 5%, e.g. 0.1 to 3%, e.g. 0.1 to 1%, e.g. 0.5 to 1%, by weight of the stabilizer, e.g. cyclodextrin, based on the total weight of the composition. For example the composition of the invention may contain about 5%, e.g. about 4%, e.g. about 3%, e.g. about 2.5%, e.g. about 2%, e.g. about 1.5%, e.g. about 1%, e.g. about 0.5% by weight of the stabilizer, e.g. cyclodextrin, based on the total weight of the composition, e.g. the final product for oral administration or an intermediate form thereof.

According to the invention, the stabilizer, e.g. the cyclodextrin, may be present in an amount about 7, e.g. about 6, e.g. about 5 times, e.g. about 4 times (weight ratios) greater than the amount of the S1P receptor modulator of the invention, e.g. than the amount of 2-amino-2-[2-(4-octylphenyl)ethyl]propane-1,3-diol or a pharmaceutically acceptable salt thereof, in a weight to weight ratio. For example, the amount of the stabilizer, e.g. the cyclodextrin, may be about 5 time higher, e.g. four times higher, e.g. three times higher, than the amount of the S1P receptor modulator of the invention, e.g. than the amount of 2-amino-2-[2-(4-octylphenyl)ethyl]propane-1,3-diol in free form or as a pharmaceutically acceptable salt thereof, e.g. 2-amino-2-[2-(4-octylphenyl)ethyl]propane-1,3-diol hydrochloride, in a weight to weight ratio.

According to the invention, the stabilizer, e.g. the cyclodextrin, may be present in an amount about 0 to 4 times, e.g. about 0.2 to 3 times, e.g. about 0.4 to 3 times, e.g. about 0.4 times, e.g. about 1 time, e.g. about 1.5 times, e.g. about 2 times, e.g. about 2.5 times, e.g. about 3 times, e.g. about 3.5 times (molar ratios) greater than the amount of the S1P receptor modulator of the invention, e.g. than the amount of 2-amino-2-[2-(4 octylphenyl)ethyl]propane-1,3-diol or a pharmaceutically acceptable salt thereof, in a molar to molar ratio. For example, the amount of the stabilizer, e.g. the cyclodextrin, may be about 3 times or 2 times higher, than the amount of the S1P receptor modulator of the invention, e.g. than the amount of 2-amino-2-[2-(4-octylphenyl)ethyl]propane-1,3-diol or a pharmaceutically acceptable salt thereof, in a molar to molar ratio. In one embodiment the molar ratio of the cyclodextrin to 2-amino-2-[2-(4-octylphenyl)ethyl]propane-1,3-diol in free or as a pharmaceutically acceptable salt thereof, e.g. as hydrochloride, is of about 0.6 to 1.2, e.g. is about 0.7, e.g. about 0.8, e.g. about 0.9, e.g. about 1.0, e.g. about 1.1, e.g. about 1.2.

According to the invention, the filler may be selected from a sugar alcohol, microcrystalline cellulose (e.g. Avicel®), methylcellulose, hydroxypropylcellulose, hydroxypropyl methylcellulose, starch (e.g. corn starch, pregelatinized starch), dicalcium phosphate, and mixture thereof.

In a specific embodiment of the invention, the filler is selected from a sugar alcohol, microcrystalline cellulose (e.g. Avicel®) and mixture thereof, for example the filler consists of one or more sugar alcohol or a mixture of one sugar alcohol with microcrystalline cellulose, e.g. a mixture of mannitol with microcrystalline cellulose, e.g. mannitol with Avicel® According to the invention, the weight ratio sugar alcohol (e.g. mannitol or mixture of mannitol with another sugar alcohol) to microcrystalline cellulose may be of about 5:95, e.g. about 10:90, e.g. about 15:85, e.g. about 20:80; e.g. about 25:75; e.g. about 30:70; e.g. about 35:65; e.g. about 40:60; e.g. about 45:55; e.g. about 50:50; e.g. about 55:45; e.g. about 60:50; e.g. about 65:45; e.g. about 70:00. In a specific embodiment the weight ratio mannitol: Avicel is of about 10:90, e.g. about 15:85, e.g. about 20:80; e,g, about 25:75, e.g. about 30:70, e.g. about 35:65.

In another embodiment, the filler comprises a mixture of one or more sugar alcohol with another filler as mentioned above. For example the filler is a mixture of one or more sugar alcohol with a second component selected from methylcellulose, hydroxypropylcellulose, and hydroxypropyl methylcellulose; e.g. the filler is a mixture of one or more sugar alcohol with hydroxypropylcellulose. In one specific example, the filler comprises a mixture of mannitol and hydroxypropylcellulose.

In another embodiment of the invention, the filler is or comprises starch, e.g. corn starch or pregelatinized starch or a mixture thereof. For example, the weight ratio sugar alcohol (e.g. mannitol or mixture of mannitol with another sugar alcohol) to starch (e.g. corn starch or pregelatinized starch or a mixture thereof) is of about 50:50; e.g. of about 55:45; e.g. of about 60:40; e.g. of about 65:35; e.g. of about 70:30; e.g. of about 75:25; e.g. of about 80:20; e.g. of about 85:15; e.g. of about 90:10. In a specific embodiment the weight ratio mannitol:starch, e.g. mannitol: corn starch or pregelatinized starch is of about 55:45; e.g. of about 60:40; e.g. of about 65:35; e.g. of about 70:30; e.g. of about 75:25; e.g. of about 80:20; e.g. of about 85:15.

The filler may be present in an amount of from about 0.1 to about 90% by weight, e.g. about 1 to about 30%, e.g. about 10 to about 30% by weight; e.g. about 15 to about 30% by weight; e.g. about 20 to about 30% by weight, e.g. about 10%, e.g. about 15%, e.g. about 20%, e.g. about 25%, e.g. about 30%, e.g. about 35%, e.g. about 40%, e.g. about 45%, e.g. about 50%, e.g. about 55%, e.g. about 60%, e.g. about 65%, by weight, based on the total weight of the composition, e.g. in the final product or an intermediate form thereof.

According to the invention, the disintegrants may be selected from crosspovidone, starch (e.g. corn starch, pregelatinised starch or mixture thereof), crosscarmellose sodium and mixture thereof. In one example, the disintegrant may comprise about 1 to 6 weight %, e.g. 2 to 5 weight %, e.g. 3 to 4 weight % of crosspovidone. It may comprise about 4 to 12 weight %, e.g. about 5 to 10 weight %, e.g. about 6 to 8 weight % of starch (e.g. corn starch, pregelatanised starch or mixture thereof). The desintegrant may comprise In one embodiment, the disintegrant may comprise a mixture of crosspovidone, pregelatanised starch and crosscarmellose sodium. For example, it may comprise about 5 to 30 weight %, e.g. about 10 to 25 weight %, e.g. about 15 to 20 weight % of crosscarmellose sodium).

According to the invention, the sugar alcohol may be selected from mannitol, maltitol, inositol, xylitol, lactitol, and mixture thereof. For example, the sugar alcohol is a substantially non-hygroscopic sugar alcohol, e.g. mannitol, e.g. D-mannitol.

A single sugar alcohol may be used, or a mixture of two or more sugar alcohols, e.g. a mixture of mannitol and xylitol, e.g. in a ratio of 1:1 to 4:1.

In a particular embodiment, the sugar alcohol is prepared from a spray-dried composition, e.g. mannitol composition, having a high specific surface area. The use of this type of mannitol composition may assist in promoting uniform distribution of the S1P receptor modulator throughout the mannitol in the composition. A higher surface area may be achieved by providing a sugar alcohol, e.g. mannitol, preparation consisting of particles having a smaller mean size and/or a rougher surface on each particle. The use of a spray-dried sugar alcohol, e.g. mannitol, e.g. with a mean particle size of 300 μm or less, has also been found to improve compressibility and hardness of tablets formed from the composition.

In one embodiment of the invention, the single point surface area of the sugar alcohol preparation, e.g. mannitol, is 1 to 7 m$^2$/g, e.g. 2 to 6 m$^2$/g or 3 to 5 m$^2$/g. The mannitol preparation may suitably have a mean particle size of 10 to 400 μm, e.g. 10 to 300 μm, e.g. 150 to 250 μm. For example, the mannitol of the invention may have a mean particle size of 60 μM, 120 μM, 180 μM, 200 μM, 300 μM or 400 μM.

For example, the mannitol may have particle of 60 μm in average, or the mannitol may be Parteck M200. In a specific embodiment, a mixture of mannitol can be used, e.g. a mixture of mannitol (60 μm) and mannitol (180 μm), or mannitol (60 μm) and mannitol (120 μm). For example, the mannitol can be a mixture of mannitol (200 μm) with another mannitol, e.g. with mannitol (180 μm), mannitol (60 μm), mannitol (120 μm) or a mixture thereof.

The ratios Mannitol (60 μm): Mannitol (180 μm) may vary from e.g. 1:0 to 2:0, e.g. from 1:2 to 1:5. For example, it may be about 20% of Mannitol (60 μm): 70% of Mannitol (180 μm); e.g. about 30% of Mannitol (60 μm): 60% of Mannitol (180 μm); e.g. about 40% of Mannitol (60 μm): 50% of Mannitol (180 μm).

The ratios Mannitol (200 μm): other mannitol (e.g. Mannitol 180 μm) may vary from e.g. 1:0 to 2:0. For example, it may be about 20% of Mannitol (200 μm): 80% of the other forms of mannitol; e.g. about 30% of Mannitol (200 μm): 70% of the other forms of mannitol; e.g. about 40% of Mannitol (60 μm): 60% of the other forms of mannitol.

The mannitol may have a bulk density of 0.4 to 0.6 g/mL, e.g. 0.45 to 0.55 g/mL.

The composition may comprise 20 to 99.99% by weight; e.g. 30 to 99.99% by weight; e.g. 40 to 99.99% by weight; e.g. 50 to 99.99% by weight; e.g. 60 to 99.99% by weight; e.g. 70 to 99.99% by weight; e.g. 75 to 99.99% by weight; e.g. 20 to 60% by weight; e.g. 25 to 55% by weight 30 to 50% by weight; e.g. about 20% by weight; e.g. 85 to 99.9%, e.g. 90 to 99.5%, e.g. 92 to 97%, e.g. 93 to 96% by weight; of the sugar alcohol, e.g. of the mannitol, on the total weight of the composition, e.g. of the final product suitable for oral administration or an intermediate form thereof. For example, it may comprise about e.g. about 25% by weight; e.g. about 30% by weight; e.g. about 35% by weight; e.g. about 40% by weight; e.g. about 45% by weight; e.g. about 50% by weight; e.g. about 55% by weight; e.g. about 60% by weight, e.g. about 70% by weight, e.g. about 80% by weight e.g. about 90% by weight, e.g. about 92% by weight, e.g. about 94% by weight, e.g. about 95% by weight, e.g. about 96% by weight, of the sugar alcohol, e.g. of the mannitol.

The composition preferably further comprises a lubricant. Suitable lubricants include stearic acid, magnesium stearate, calcium stearate, zinc stearate, glyceryl palmitostearate, sodium stearyl fumarate, canola oil, hydrogenated vegetable oil such as hydrogenated castor oil (e.g. Cutina® or Lubriwax® 101), mineral oil, sodium lauryl sulfate, magnesium oxide, colloidal silicon dioxide, silicone fluid, polyethylene glycol, polyvinyl alcohol, sodium benzoate, talc, poloxamer, or a mixture of any of the above. For example the lubricant comprises magnesium stearate, hydrogenated castor oil, mineral oil, colloidal silicon dioxide, polyethylene glycol or a mixture thereof, e.g. magnesium stearate, hydrogenated castor oil, mineral oil or a mixture thereof. In a specific embodiment the lubricant consists of magnesium stearate, hydrogenated castor oil, mineral oil or a mixture thereof, e.g. consists of magnesium stearate or a mixture of magnesium stearate with another lubricant.

The composition preferably comprises 0.01 to 5% by weight of the lubricant, e.g. of magnesium stearate, for example 0.5 to 3% by weight, 1 to 2% by weight, e.g. about 3% by weight, e.g. about 2% by weight, about 1% by weight, about 0.5% by weight about 0.05% by weight, based on the total weight of the composition.

The composition may comprise one or more further excipients such as a binder. The binder may be selected from polyvinyl pyrrolidone, methylcellulose, hydroxypropyl cellulose, hydroxypropylmethyl cellulose, and mixture thereof. When used, the binder may be included in an amount of 1 to 8%, e.g. 3 to 6% by weight, based on the total weight of the composition.

The use of a binder increases the granule strength of the formulation, which is particularly important for fine granulations. Microcrystalline cellulose and methylcellulose are particularly preferred where a high tablet hardness and/or longer disintegration time is required. Hydroxypropyl cellulose may be preferred where faster distintegration is required. Where appropriate, xylitol may also be added as an additional binder, for example in addition to microcrystalline cellulose, e.g. in an amount up to 30% by weight, e.g. up to 20% by weight; e.g. up to 10% by weight of the sugar alcohol, e.g. mannitol or xylitol or mixture thereof.

The composition of the invention refers to a solid composition suitable for oral administration, or to an intermediate form thereof, e.g. a formulation can be used to prepare a solid composition suitable for oral administration The composition may be in the form of a soft gel, powder, granule or pellets or a unit dosage form, for example as a tablet or capsule, e.g. a friezed dried tablet. The compositions of the present invention are well-adapted for encapsulation into an orally administrable capsule shell, particularly a hard gelatin shell or a HPMC (hypromellose) capsule. For example, it can be compositions that are filled using the liquid dispensing technology for hard gelatin capsule. The solution containing the compound of the invention, may be dispensed in a capsule which is prefilled with the sugar alcohol as herein above defined, e.g. mannitol.

Alternatively the compositions may be compacted into tablets. The tablets may optionally be coated, for instance with talc or a polysaccharide (e.g. cellulose) or hydroxypropylmethylcellulose coating.

The composition of the invention does not refer to an injection or another parenteral composition.

Where the pharmaceutical composition is in unit dosage form, each unit dosage may contain 0.01 mg to 5 mg of the S1P receptor modulator, e.g. 0.01 mg to 1 mg, e.g. 0.01 mg to 0.7 mg, e.g. 0.03 to 0.50 mg, e.g. 0.05 mg to 0.50 mg, e.g. 0.06 mg to 0.50 mg, e.g. 0.10 mg to 0.50 mg, e.g. 0.12 to 0.50 mg, e.g. 0.13 mg to 0.50 mg, e.g. 0.14 mg to 0.50 mg, e.g. 0.15 mg to 0.50 mg, e.g. 0.16 mg to 0.50 mg, e.g. 0.17 mg to 0.50 mg, e.g. 0.18 mg to 0.50 mg, e.g. 0.19 mg to 0.50 mg, e.g. 0.20 mg to 0.50 mg, e.g. 0.21 mg to 0.50 mg, e.g. to 0.22 mg to 0.50 mg, e.g. to 0.23 mg to 0.50 mg e.g. to 0.24 mg to 0.50 mg e.g. to 0.25 mg to 0.50 mg, e.g. to 0.26 mg to 0.50 mg, e.g. to 0.27 mg to 0.50 mg e.g. to 0.28 mg to 0.50 mg, e.g. to 0.29 mg to 0.50 mg, e.g. to 0.30 mg to 0.50 mg, e.g. to 0.32 mg to 0.50 mg, e.g. to 0.34 mg to 0.50 mg.

In another embodiment, each unit dosage may contain 0.01 mg to 0.40 mg, e.g. 0.02 mg to 0.40 mg, e.g. 0.03 mg to 0.40 mg, e.g. 0.06 mg to 0.40 mg, e.g. 0.10 mg to 0.40 mg, e.g. 0.12 mg to 0.40 mg, e.g. 0.13 mg to 0.40 mg, e.g. 0.14 mg to 0.40 mg, e.g. 0.15 mg to 0.40 mg, e.g. 0.16 mg to 0.40 mg, e.g. 0.17 mg to 0.40 mg, e.g. 0.18 mg to 0.40 mg, e.g. 0.20 mg to 0.40 mg, e.g. 0.22 mg to 0.40 mg, e.g. 0.25 mg to 0.40 mg, e.g. 0.30 mg to 0.40 mg, e.g. 0.35 mg to 0.40 mg.

In a further embodiment, each unit dosage may contain 0.050 mg to 0.350 mg, e.g. 0.050 mg to 0.325 mg, e.g. 0.060 mg to 0.350 mg, e.g. 0.060 mg to 0.325 mg, e.g. 0.125 mg to 0.350 mg, e.g. 0.125 mg to 0.325 mg.

In a specific embodiment, each unit dosage contains about 0,125 mg, about 0.250 mg or about 0.500 mg.

In another specific embodiment, each unit dosage contains either about 0.03 mg, about 0.06 mg, about 0.125 mg, about 0.250 mg, about 0.325 mg or about 0.500 mg.

For example, when is in unit dosage form, each unit dosage of the composition of the invention may contain about 0.50 mg, e.g. about 0.40 mg, e.g. about 0.30 mg, e.g. about 0.25 mg, e.g. about 0.20 mg, e.g. about 0.15 mg, e.g. about 0.14 mg, e.g. about 0.13 mg, e.g. about 0.12 mg, e.g. about 0.11 mg, e.g. about 0.10 mg, e.g. about 0.06 mg, e.g. about 0.05 mg, e.g. about 0.04 mg, e.g. about 0.03 mg, e.g. about 0.02 mg, e.g. about 0.01 mg, e.g. about 0.375 mg, e.g. 0.325 mg, e.g. 0.175 mg, e.g. about 0.135 mg, e.g. about 0.125 mg, e.g. about 0.115 mg, e.g. about 0.105 mg.

For example, the pharmaceutical composition of the invention is in unit dosage for, e.g. is a capsule or tablet, and comprises about 0.06 mg, or about 0.125 mg, or about 0.250 mg, or about 0.325 mg or about 0.375 mg of the S1P receptor modulator of the invention, e.g. 2-amino-2-[2-(4-octylphenyl)ethyl]propane-1,3-diol hydrochloride.

The compositions of the invention may show good stability characteristics as indicated by standard stability trials, for example having a shelf life stability of up to one, two or three years, and even longer. As herein defined, stable pharmaceutical compositions refer to pharmaceutical compositions containing no impurities or impurities that are present in an amount acceptable, e.g. on storage at room temperature, in particular in view of the Regulatory Health Authorities Regulations and requirements. Stability characteristics may be determined, e.g. by measuring decomposition products by HPLC analysis after storage for particular times, at particular temperatures, e.g. 20°, 40° or 60° C., and/or under high humidity conditions.

The pharmaceutical compositions of the present invention may be produced by standard processes, for instance by conventional mixing, granulating, sugar-coating, dissolving or lyophilizing processes. Procedures which may be used are known in the art, e.g. those described in L. Lachman et al. The Theory and Practice of Industrial Pharmacy, 3rd Ed, 1986, H. Sucker et al, Pharmazeutische Technologie, Thieme, 1991, Hagers Handbuch der pharmazeutischen Praxis, 4th Ed. (Springer Verlag, 1971) and Remington's Pharmaceutical Sciences, 13th Ed., (Mack Publ., Co., 1970) or later editions.

In one aspect, the present invention relates to a process for producing a pharmaceutical composition, comprising:
(a) mixing the stabilizer, e.g. a cyclodextrin, with S1P receptor modulator; and optionally milling and/or granulating the mixture obtained
(b) mixing the filler, e.g. the sugar alcohol, e.g. mannitol; optionally milling and/or granulating the mixture obtained;
(c) optionally milling and/or granulating the mixture obtained in (b); and
(d) mixing the milled and/or granulated mixture obtained in (b) or (c) with a lubricant.

In step (b), the filler, e.g. the sugar alcohol, e.g. the mannitol, may optionally be milling and/or granulated before been mixed to the mixture obtained in step (a).

In another embodiment of the invention, the composition of the invention may be produced by a process, comprising:
(a) mixing the stabilizer, e.g. a cyclodeytrin, with S1P receptor modulator; and optionally milling and/or granulating the mixture obtained
(a1) mixing the binder (e.g. hydroxypropyl cellulose) of the invention with a sugar alcohol, e.g. mannitol; and optionally milling and/or granulating the mixture obtained;
(b) mixing the mixtures obtained in step (a) and (a1);
(c) optionally milling and/or granulating the mixture obtained in (b); and
(d) mixing the milled and/or granulated mixture obtained in (b) or (c) with a lubricant.

By using this process, a preparation having a good level of content and blend uniformity (i.e. a substantially uniform distribution of the S1P receptor modulator throughout the composition), dissolution time and stability is obtained.

The S1P receptor modulator, e.g. 2-amino-2-[2-(4-octylphenyl)ethyl]propane-1,3-diol, hydrochloride, may optionally be micronized, and/or pre-screened, e.g. with a 400 to 500 μm mesh screen, before step (a) in order to remove lumps. The mixing step (a) may suitably comprise blending the S1P receptor modulator and the filler, e.g. sugar alcohol, e.g. mannitol in any suitable blender or mixer for e.g. 100 to 400 revolutions.

The process may be carried out by dry mixing the components. In this embodiment the milling step (a), (a1), or (c) may suitably comprise passing the mixture obtained in (a) or (a1) through a screen, which preferably has a mesh size of 400 to 500 μm. Process step (a) may comprise the step of mixing the total amount of S1P receptor modulator at first with a cyclodextrin in order to form a pre-mix. Subsequently the required amount of sugar alcohol is added to the pre-mix.

Step (a), (a1) or (c) may also comprise the step of adding a binder solution, e.g. methylcellulose and/or xylitol, e.g. an aqueous solution, to the mixture. Alternatively the binder is added to the mix dry and water is added in the granulation step.

The milled mixture obtained in (a) or (a1) may optionally be blended once more before mixing with the lubricant. The lubricant, e.g. magnesium stearate, is preferably pre-screened, e.g. with a 800 to 900 μm screen, before mixing.

Alternatively, a wet granulation process may be employed. In this embodiment, the S1P receptor modulator is preferably solubilized in a solvent with the stabilizer, e.g. cyclodextrin and sprayed on the dry-mix of the desired filler, e.g. sugar alcohol, e.g. mannitol. The obtained filler/S1P receptor modulator mixture, e.g. sugar alcohol/S1P receptor modulator mixture, e.g. mannitol/S1P receptor modulator mixture, may then be dry-mixed with another binder such as e.g. hydroxypropyl cellulose or hydroxypropylmethyl cellulose. The solvent is then added and the mixture granulated, e.g. using an automated granulator. The granulation is then dried and milled. The solvent may be water.

Alternatively, a spray coating process may be employed. In this embodiment the DS is solution (DS+CD) is sprayed on sugar beads or mannitol beads, the solvent is evaporate and the dried beads are than encapsulated in hard gelatin or HPMC capsules. Solvents used to prepare the DS solution could be water (aqueous) or Ethanol (non-aqueous).

If desirable, an additional amount of binder may be added in step (d) to the mixture obtained in (b).

The process may comprise a further step of tabletting or encapsulating the mixture obtained in (d), e.g. into a hard gelatin capsule using an automated encapsulation device. The capsules may be coloured or marked so as to impart an individual appearance and to make them instantly recognizable. The use of dyes can serve to enhance the appearance as well as to identify the capsules. Dyes suitable for use in pharmacy typically include carotinoids, iron oxides, and chlorophyll. Preferably, the capsules of the invention are marked using a code.

According to the invention, there is provided a process for producing a solid composition for oral administration of 2-amino-2-[2-(4-octylphenyl)ethyl]propane-1,3-diol in free form, in a pharmaceutically acceptable salt form or in a phosphate derivative form, comprising the steps of (i) mixing a compound selected from 2-amino-2-[2-(4-octylphenyl)ethyl]propane-1,3-diol, a pharmaceutically acceptable salt thereof, and a phosphate derivative thereof, with a stabilizer, e.g. a cyclodextrin, in a solvent; (ii) mixing a filler, e.g. sugar alcohol, to the mixture obtained in step (i); (iii) adding the solvent; (iv) granulating, (v) drying, milling, blending, and (vi) optionally tabletting or encapsulating.

Optionally a binder may be mixed, e.g. dry mixed, to the mixture obtained in step (ii) and/or step (iii). In a specific embodiment, in step (ii) the used filler, e.g. the sugar alcohol, e.g. mannitol, is spray-dried.

By using this process, a preparation having a good level of content and blend uniformity (i.e. a substantially uniform distribution of the drug throughout the composition), and stability is obtained.

The pharmaceutical compositions of the present invention are useful, either alone or in combination with other active agents, for the treatment and prevention of conditions e.g. as disclosed in U.S. Pat. No. 5,604,229, WO 97/24112, WO 01/01978, U.S. Pat. No. 6,004,565, U.S. Pat. No. 6,274,629 and JP-14316985, the contents of which are incorporated herein by reference.

In particular, the pharmaceutical compositions are useful for:
a) treatment and prevention of organ or tissue transplant rejection, for example for the treatment of the recipients of heart, lung, combined heart-lung, liver, kidney, pancreatic, skin or corneal transplants, and the prevention of graft-versus-host disease, such as sometimes occurs following bone marrow transplantation; particularly in the treatment of acute or chronic allo- and xenograft rejection or in the transplantation of insulin producing cells, e.g. pancreatic islet cells;

b) treatment and prevention of autoimmune disease or of inflammatory conditions, e.g. chronic long term diseases, e.g. multiple sclerosis, arthritis (for example rheumatoid arthritis), inflammatory bowel disease, hepatitis, etc.;

Multiple sclerosis takes several forms, with new symptoms occurring either in discrete attacks (relapsing forms) or slowly accumulating over time (progressive forms). As herein defined, multiple sclerosis refers, but is not limited to, relapsing remitting multiple sclerosis (RRMS) or primary progressive multiple sclerosis (PPMS), e.g. RRMS.

According to the present invention the terms "treatment" or "treat" refer to both prophylactic or preventive treatment as well as curative or disease-modifying treatment, including treatment of patients at risk of contracting the disease or disorder, or suspected to have contracted the disease or disorder, as well as patients who are ill or have been diagnosed as suffering from the disease or disorder.

As herein defined, treating multiple sclerosis refers to, but is not limited to, reducing the frequency of clinical exacerbations, delaying the progression of symptoms or disorders associated with multiple sclerosis or delaying the accumulation of physical disability induced by multiple sclerosis.

Symptoms or disorders associated with multiple sclerosis encompass neurological symptoms, physical and cognitive disability and neuropsychiatric disorders.

Accordingly, in further aspects the present invention provides:

1. A composition as defined above, for use in treating or preventing a disease or condition as defined above.
2. A method of treating a subject in need of immunomodulation, comprising administering to the subject an effective amount of a composition as defined above.
3. A method of treating or preventing a disease or condition as defined above, comprising administering to the subject a composition as defined above.
4. Use of a pharmaceutical composition as defined above for the preparation of a medicament for the prevention or treatment of a disease or condition as defined above.

The invention will now be described with reference to the following specific embodiments.

Example 1

FTY720 is dissolved in water to form approximately 20 percent (solution A). HP-3 CD is dissolved in water to form approximately 15 percent (solution B). Mannitol is added in a low shear granulator and sprayed solutions A and B. The granulated material thus obtained is dried in a tray dryer set at 60° C. The dried granules are then milled through a Frewitt mill attached with a 18 mesh screen. The milled granules are blended with magnesium stearate in a bin blender.

The lubricated granules are compressed to form tablets of the desired dose of 0.04 mg, and then encapsulated to achieve the desired dose of 0.125 mg, containing:

TABLE 1

| Ingredients | Quantity per 0.040 mg mini-tablet (mg) | Quantity per 0.125 mg capsule (mg) |
|---|---|---|
| FTY720 HCl[1] | 0.0448 | 0.140 |
| Mannitol USP | 3.755 | 11.735 |
| Hydroxy propyl beta cyclodextrin (HP-β CD) | 0.120 | 0.375 |
| Magnesium Stearate | 0.040 | 0.125 |

[1] 1.0 part of FTY720 is equivalent to 1.119 part of FTY720 HCl salt

Example 2

The composition with Hydroxy-beta-cyclodextrin in Example 1 is used to process the bulk powder for mini tablets and capsules.

TABLE 2

Blend uniformity assay results with total degradation products

| % FTY720 Assay | Total Degradation | Mass Balance | Range/Average |
|---|---|---|---|
| 96.9 | 0.1 | 97.1 | 93.8-99.2% |
| 95.7 | 0.1 | 95.9 | RSD: |
| 98.9 | 0.3 | 99.2 | 2.3 |
| 93.6 | 0.2 | 93.8 | |

Table 2 shows blend uniformity results for the final blend with an RSD of 2.3% indicating no segregation issues after final blending. The final blend is then compressed in mini tablets and encapsulated.

The compressed tablets are of 4 mg in weight delivering a dose of 40 micrograms of drug.

TABLE 3 stability under different conditions including stress condition of 50° C./75% RH.

| | % FTY720 Assay | | Total Deg | | Mass Balance | |
|---|---|---|---|---|---|---|
| Stability Condition/ Time Points | with HP-β CD | without CD | with HP-β CD | without CD | with HP-β CD | without CD |
| 0 week | 100.19 | 95.02 | 0 | 0.0 | 100.2 | 95.0 |
| 50 D—Dry/2 week | 98.97 | 94.12 | 0.5 | 0.7 | 99.4 | 94.8 |
| 50 D—75% RH/2 week | 96.04 | 90.88 | 1.5 | 1.2 | 97.6 | 92.1 |
| 50 D—75% RH/12 wk | 104.25 | 100.23 | 2.5 | 7.0 | 106.7 | 107.2 |
| 25 D/60% RH/4 week | 100.20 | 93.86 | 1.2 | 0.5 | 101.4 | 94.3 |
| 50 D—Dry/4 week | 99.04 | 93.99 | 0.6 | 1.4 | 99.6 | 95.4 |
| 50 D—75% RH/4 week | 95.94 | 87.23 | 1.4 | 2.4 | 97.4 | 89.6 |

CD = cyclodextrin

The data below shows a total degradation product of 1.4% at 50° C./75% RH for 4 weeks in the formulation with HP-β CD.

The capsules are encapsulated with a fill weight of 14 mg to deliver a dose of 125 micrograms each. The table 4 summarizes the data for stability at different conditions including the stress conditions of 50° C./75% RH (Relative Humidity)

TABLE 4

| Stability Condition/ Time Points Batch # | % FTY720 Assay | | % Total Deg | | Mass Balance | |
|---|---|---|---|---|---|---|
| | with HP-β CD | without CD | with HP-β CD | without CD | with HP-β CD | without CD |
| 0 week | 110.04 | 108.48 | 0 | 0 | 110.0 | 108.5 |
| 50 D—Dry/2 week | 111.07 | 110.98 | 0.0 | 0.2 | 111.1 | 111.2 |
| 50 D—75% RH/2 week | 108.94 | 106.09 | 0.3 | 0.7 | 109.2 | 106.8 |
| 5 D/12 wk | 110.75 | 109.89 | 0.4 | 0.1 | 111.2 | 110.0 |
| 25 D/60% RH/12 wk | 113.01 | 112.46 | 0.3 | <LOQ | 113.3 | 112.5 |
| 50 D—Dry/12 wk | 110.47 | 106.29 | 0.4 | 1.2 | 110.9 | 107.4 |
| 50 D—75% RH/12 wk | 104.25 | 100.23 | 2.5 | 7.0 | 106.7 | 107.2 |

The data shows a total degradation product of 2.5% in the formulation with HP-β CD.

Stability results in both tablets and capsules are indicative of increased stability of FTY720 in the drug product.

Example 3

Hard gelatin capsules containing FTY720 are prepared as follow: HP-CD and FTY720 are dissolved in water to form approximately 20 percent (solution A). HPC is dissolved in water to form approximately 7 percent (solution B). Mannitol is added to a fluid bed drier and sprayed with solutions A and B. The granulated material is than dried at a set inlet temperature of 65° C. in the fluid bed drier. The dried granules are then milled through a Frewitt mill attached with a 18 mesh screen. The milled granules are blended with magnesium stearate in a bin blender. The lubricated granules are encapsulated to obtain the desired dose of 0.03 mg.

The same process is used to prepare the other capsules whose components are listed below:

TABLE 5

Composition of FTY720 0.03, 0.06 mg, 0.125 mg and 0.25 mg capsules

| Ingredient | 0.03 mg capsule (mg) | 0.06 mg capsule (mg) | 0.125 mg capsule (mg) | 0.25 mg capsule (mg) |
|---|---|---|---|---|
| FTY720 HCl[1] | 0.0336 | 0.0671 | 0.140 | 0.280 |
| Hydroxypropylcellulose | 0.438 | 0.875 | 0.875 | 1.750 |
| Hydroxypropyl-beta-cyclodextrin | 0.145 | 0.289 | 0.301 | 0.603 |
| Mannitol | 11.759 | 23.5189 | 23.434 | 46.868 |
| Magnesium Stearate[2] | 0.125 | 0.2500 | 0.250 | 0.500 |
| Water, purified[3] | — | — | — | — |
| Capsule fill weight (theoretical weight) | 12.50 | 25.00 | 25.00 | 50.00 |
| Empty capsule shell Weight of capsule shell | 48.00 | 48.00 | 48.00 | 48.00 |
| Total weight | 60.50 | 73.00 | 73.00 | 98.00 |

[1]The molecular weight ratio of FTY720 HCl to FTY720 base is approximately 1.12 to 1.0
[2]Vegetable origin
[3]Used as a granulating aid and removed during processing.

The invention claimed is:

1. A solid pharmaceutical composition suitable for oral administration, comprising
   a) a first compound selected from 2-amino-2-[2-(4-octyl-pheny)hethyl]propane-1,3-diol, a pharmaceutically acceptable salt thereof, and a phosphate derivative thereof,
   b) a filler, and
   c) a stabilizer against the inducement of degradation products, wherein the stabilizer comprises a cyclodextrin or a derivative thereof,
   wherein the cyclodextrin or derivative thereof is natural cyclodextrin, a branched cyclodextrin, an alkyl-cyclodextrin or a hydroxyalkyl-cyclodextrin, and wherein the pharmaceutical composition is in unit dosage form, each unit comprising less than 0.5 mg of the first compound.

2. The composition according to claim 1, wherein the filler comprises a sugar alcohol.

3. The composition according to claim 1, further comprising a binder.

4. The composition according to claim 1, further comprising a lubricant.

5. The composition according to claim 1, wherein the stabilizer comprises hydroxypropyl-beta-cyclodextrin.

6. The composition according to claim 1, wherein the first compound is 2-amino-2-[2-(4-octylphenyl)ethyl]propane-1, 3-diol or a pharmaceutically acceptable salt thereof.

7. The composition according to claim 2, wherein the sugar alcohol is mannitol.

8. The composition according to claim 3, wherein the binder is hydroxypropyl cellulose.

9. The composition according to claim 1, wherein the cyclodextrin or derivative thereof is selected from the group consisting of α-cyclodextrin; β-cyclodextrin, γ-cyclodextrin; hydroxypropyl-cyclodextrin, sulfobutylether β-cyclodextrin, dodecakis-2,6,O-methyl-α-cyclodextrin, tetradecakis-2,6,O-methyl-β-cyclodextrin, hexadecakis-2,6,O-methyl-γ-cyclodextrin, tetradecakis-2,6,O-ethyl-β-cyclodextrin, α-cyclodextrin partially etherized with 2-hydroxypropyl, β-cyclodextrin partially etherized with 2-hydroxypropyl, branched α-cyclodextrin, and branched β-cyclodextrin where glucose or maltose has been bound via α-1,6 glucoside bond.

10. The composition according to claim 4, wherein the lubricant is magnesium stearate.

11. A method of reducing the frequency of clinical exacerbations, delaying the progression of symptoms or disorders associated with multiple sclerosis or delaying the accumulation of physical disability induced by multiple sclerosis in a patient in need thereof, comprising administering a therapeutically effective amount of the solid pharmaceutical composition according to claim 1.

* * * * *